US010537897B2

(12) United States Patent
Tsao et al.

(10) Patent No.: US 10,537,897 B2
(45) Date of Patent: Jan. 21, 2020

(54) GRINDING MACHINE AND A SLIGHT GYRATION MODULE

(71) Applicant: INDUSTRIAL TECHNOLOGY RESEARCH INSTITUTE, Hsin-Chu (TW)

(72) Inventors: Jia-Huey Tsao, Taipei County (TW); SHow-Ying Yang, Hsinchu (TW); Yu-Chi Chang, Taipei (TW)

(73) Assignee: INDUSTRIAL TECHNOLOGY RESEARCH INSTITUTE, Hsin-Chu (TW)

( * ) Notice: Subject to any disclaimer, the term of this patent is extended or adjusted under 35 U.S.C. 154(b) by 571 days.

(21) Appl. No.: 15/378,419

(22) Filed: Dec. 14, 2016

(65) Prior Publication Data

US 2018/0093274 A1 Apr. 5, 2018

(30) Foreign Application Priority Data

Sep. 30, 2016 (TW) ............................ 105131734 A

(51) Int. Cl.
*B02C 19/00* (2006.01)
*A61J 7/00* (2006.01)
(Continued)

(52) U.S. Cl.
CPC ............. *B02C 19/00* (2013.01); *A61J 7/0007* (2013.01); *B02C 17/14* (2013.01); *B02C 17/24* (2013.01)

(58) Field of Classification Search
CPC ......... B02C 19/00; B02C 17/24; B02C 17/14; A61J 7/0007; G01N 2001/2866; G01N 1/286
See application file for complete search history.

(56) References Cited

U.S. PATENT DOCUMENTS 4,775,393 A * 10/1988 Boecker .................. B02C 17/14 51/293
4,828,395 A 5/1989 Saito et al.
(Continued)

FOREIGN PATENT DOCUMENTS

CN 101650274 A 2/2010
CN 102258424 A 11/2011
(Continued)

OTHER PUBLICATIONS

CNIPA, "Office Action", dated Jan. 2, 2019, China.
Intellectual Property Office, Ministry of Economic Affairs, R. O. C, "Office Action", dated Apr. 13, 2017, Taiwan.

*Primary Examiner* — Jonathan G Riley
(74) *Attorney, Agent, or Firm* — Locke Lord LLP; Tim Tingkang Xia, Esq.

(57) ABSTRACT

A grinding machine includes a slight gyration module for driving a homogeneous container to undergo an X-axial motion and a Y-axial motion within ±1-3 mm distance, a homogeneous-stick rotation module for rotating a homogeneous stick in the homogeneous container so as to generate an eccentric motion between the homogeneous stick and the homogeneous container, and a homogeneous-stick vertical movement module for vertically moving the homogeneous stick with respect to the homogeneous container. When the homogeneous stick is lowered into the homogeneous container by the homogeneous-stick vertical movement module, an eccentric motion with a 1-3 mm radius of gyration can be activated between the homogeneous container and the homogeneous stick so as to carry out the grinding in a tiny slim space between the homogeneous container and the homogeneous stick; such that the grinding efficiency of the grinding machine can be substantially enhanced.

21 Claims, 6 Drawing Sheets

(51) Int. Cl.
*B02C 17/14* (2006.01)
*B02C 17/24* (2006.01)

(56) References Cited

U.S. PATENT DOCUMENTS

| | | | | | |
|---|---|---|---|---|---|
| 4,932,166 | A * | 6/1990 | Boecker | B02C 17/14 | 51/293 |
| 5,198,241 | A * | 3/1993 | Marcovecchio | B30B 11/005 | 100/51 |
| 5,323,655 | A * | 6/1994 | Eagan | G01N 1/286 | 73/432.1 |
| 5,785,578 | A * | 7/1998 | Thoresen | B24B 7/228 | 451/14 |
| 5,803,377 | A * | 9/1998 | Farrell | A23G 9/12 | |
| 5,824,913 | A * | 10/1998 | Pyle | B29C 43/04 | 73/818 |
| 6,113,016 | A * | 9/2000 | Vedefors | B26D 1/0006 | 241/169.1 |
| 6,205,864 | B1 * | 3/2001 | Vialletel | G01N 1/286 | 73/813 |
| 6,494,392 | B1 * | 12/2002 | Vedefors | A01G 3/002 | 241/101.78 |
| 6,739,531 | B2 | 5/2004 | Taylor | | |
| 7,270,284 | B2 | 9/2007 | Liao et al. | | |
| 8,216,528 | B2 | 7/2012 | Shomi | | |
| 8,893,995 | B2 | 11/2014 | Taghizadeh et al. | | |
| 8,967,512 | B1 | 3/2015 | Taghizadeh et al. | | |
| 9,228,924 | B2 * | 1/2016 | Jindo | G01N 1/286 | |
| 9,303,631 | B1 * | 4/2016 | Guenther | B30B 1/38 | |
| 9,346,058 | B2 | 5/2016 | Yamamoto et al. | | |
| 2002/0182990 | A1 * | 12/2002 | Thyssen | B23Q 5/04 | 451/242 |
| 2003/0066915 | A1 * | 4/2003 | Taylor | C12N 1/066 | 241/100 |
| 2005/0258285 | A1 * | 11/2005 | McCambridge | A61B 10/0096 | 241/2 |
| 2007/0262181 | A1 * | 11/2007 | Czarnek | G01N 1/286 | 241/2 |
| 2010/0208545 | A1 * | 8/2010 | Ando | B01F 5/0663 | 366/138 |
| 2013/0258800 | A1 | 10/2013 | Jindo et al. | | |
| 2014/0056762 | A1 * | 2/2014 | Giovanoli | G01N 1/286 | 422/63 |
| 2015/0165443 | A1 * | 6/2015 | Moszumanski | B02C 17/08 | 241/175 |
| 2015/0285717 | A1 * | 10/2015 | Tseng | G01N 33/56966 | 435/7.21 |
| 2017/0122845 | A1 * | 5/2017 | Logue | B01D 9/04 | |
| 2018/0064131 | A1 * | 3/2018 | Noth | A23G 9/12 | |
| 2019/0204190 | A1 * | 7/2019 | Wang | B01F 11/0008 | |

FOREIGN PATENT DOCUMENTS

| | | | | | |
|---|---|---|---|---|---|
| CN | 204079978 | U | | 1/2015 | |
| CN | 204429405 | U | | 7/2015 | |
| CN | 102971507 | B | | 11/2015 | |
| CN | 105709904 | A | | 6/2016 | |
| CN | 105797818 | B | * | 6/2016 | B02C 17/10 |
| EP | 0191941 | A1 | | 8/1986 | |
| JP | 60012122 | A | * | 1/1985 | B01F 7/1665 |
| JP | 61043982 | A | * | 3/1986 | C12M 47/08 |
| JP | 61054245 | A | * | 3/1986 | C12M 47/08 |
| JP | 62079771 | A | * | 4/1987 | C12M 47/08 |
| JP | 62121627 | A | * | 6/1987 | B01F 7/008 |
| JP | 01231930 | A | * | 9/1989 | B01F 7/00908 |
| JP | 02273533 | A | * | 11/1990 | |
| JP | 03027278 | A | * | 2/1991 | |
| TW | I422433 | B | | 1/2014 | |
| TW | I443192 | B | | 7/2014 | |
| TW | I461695 | B | | 11/2014 | |
| WO | WO-2010127434 | A1 | * | 11/2010 | B01F 3/1221 |

* cited by examiner

GRINDING MACHINE AND A SLIGHT GYRATION MODULE

CROSS REFERENCE TO RELATED APPLICATION

The present application is based on, and claims priority from, Taiwan (International) Application Ser. No. 105131734, filed on Sep. 30, 2016 the disclosure of which is hereby incorporated by reference herein in its entirety.

TECHNICAL FIELD

The present disclosure relates to a technique for enhancing grinding efficiency and homogenization performance, and more particularly to a grinding machine having a slight gyration module.

BACKGROUND

In the art, prior to processing mass vegetative asexual reproduction, pathogen detection shall be performed upon the mother body in advance so as thereby to confirm that the mother body does not carry any pathogen. Sometimes, the mother body may be negative to the pathogen examination, only because the pathogen has not been growing to reach a detective concentration. In this circumstance, if mass reproduction is still carried out, then enormous monetary loss and large-scale interactive infection might be inevitable. Currently, popular pathogen examination techniques include the enzyme-linked immunosorbent assay (ELISA) and the polymerase chain reaction (PCR) of molecular biological detection technology. However, these two techniques do have common shortcomings in labor demanding, technical dependence, poor automation and examination expense. In particular, according to current examination procedures, preparation of specimens including a grinding step is an indispensable process.

Conventional homogeneous grinding equipment mainly undergoes a manual homogenization operation upon a single tube per each cycle. Such an operation is featured in a low grinding speed, less precision.

Therefore, in view of the aforesaid shortcomings that could lead to less efficiency in testing, an improvement upon the homogenization of the specimens is definitely welcome and crucial to the art.

SUMMARY

Accordingly, the present disclosure is to provide a grinding machine that includes a slight gyration module, a homogeneous-stick rotation module and a homogeneous-stick vertical movement module.

In one embodiment of this disclosure, the slight gyration module further includes at least a gyration base, a gyration hole, a gyration arm, a rotary shaft, an X-axial sliding rack, a Y-axial sliding block, a Y-axial sliding rack, a plurality of spring members and a fixed block. The grinding machine further includes a motor, a gear pair consisted of a pinion and a gear. The rotary shaft of the slight gyration module is rotated by the motor via the gear pair.

In one embodiment of this disclosure, the homogeneous-stick rotation module further includes a rotary motor, a pulley set, a transmission belt and a rotary shaft. The homogeneous stick is connected to the rotary shaft via a connector.

In one embodiment of this disclosure, the homogeneous-stick vertical movement module further includes a supportive frame, a motor, a shaft coupler, a screw bar, a top plate, a nut and a fixed frame. A top end of the screw bar is rotationally mounted at the top plate, while a lower end of the screw bar is connected to the motor via the shaft coupler.

In one embodiment of this disclosure, the slight gyration module further includes at least a gyration base, a gyration hole, a gyration arm, a rotary shaft, an X-axial sliding rack, a Y-axial sliding block, a Y-axial sliding rack, a plurality of spring members and a fixed block. The gyration hole is a square hole having four arc-shaped corners.

The gyration arm has a free round end for constantly contacting an inner contour of the gyration hole. While the gyration arm rotates to drive the gyration base, a radius of gyration within 1-3 mm can be achieved. The radius of gyration is a difference of a length of the gyration arm and a half length of the gyration hole.

In one embodiment of this disclosure, the container carrier includes at least a carrier roof, a carrier base and a plurality of connection columns. The carrier roof and the carrier base are fixed by the plurality of connection columns and separated by a predetermined distance. Lower ends of the connection columns position fixedly the container carrier on the gyration base. The homogeneous container is held by co-axial holes located on the carrier roof and the carrier base.

In one embodiment of this disclosure, both the homogeneous container and the homogeneous stick have respective V-shape ends. While the V-shape end of the homogeneous stick is lowered to position in the homogeneous container, these two sleeving V-shape ends are separated by a tiny slim space. When the homogeneous container is positioned by the container carrier, the homogeneous stick is lowered into the homogeneous container by the homogeneous-stick vertical movement module, the homogeneous stick is rotated by the homogeneous-stick rotation module, and the slight gyration motion upon the homogeneous container is performed by the slight gyration module, then a corresponding eccentric motion would occur between the homogeneous container and the homogeneous stick so as to carry out the grinding in the aforesaid tiny slim space between the homogeneous container and the homogeneous stick. Upon such an arrangement, the grinding efficiency of the grinding machine can be substantially enhanced.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
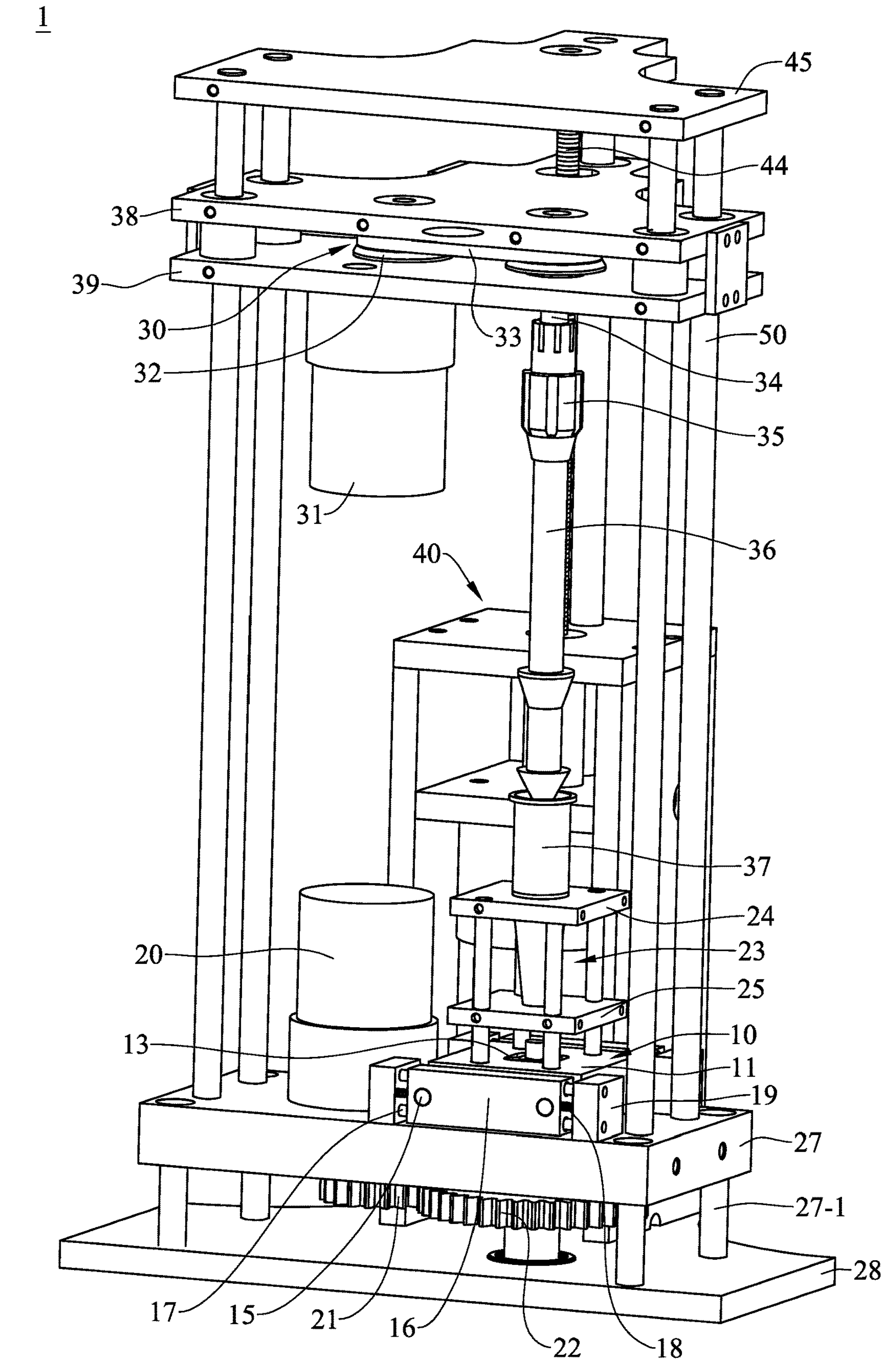
FIG. 1 is a schematic perspective view of a preferred grinding machine in accordance with the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
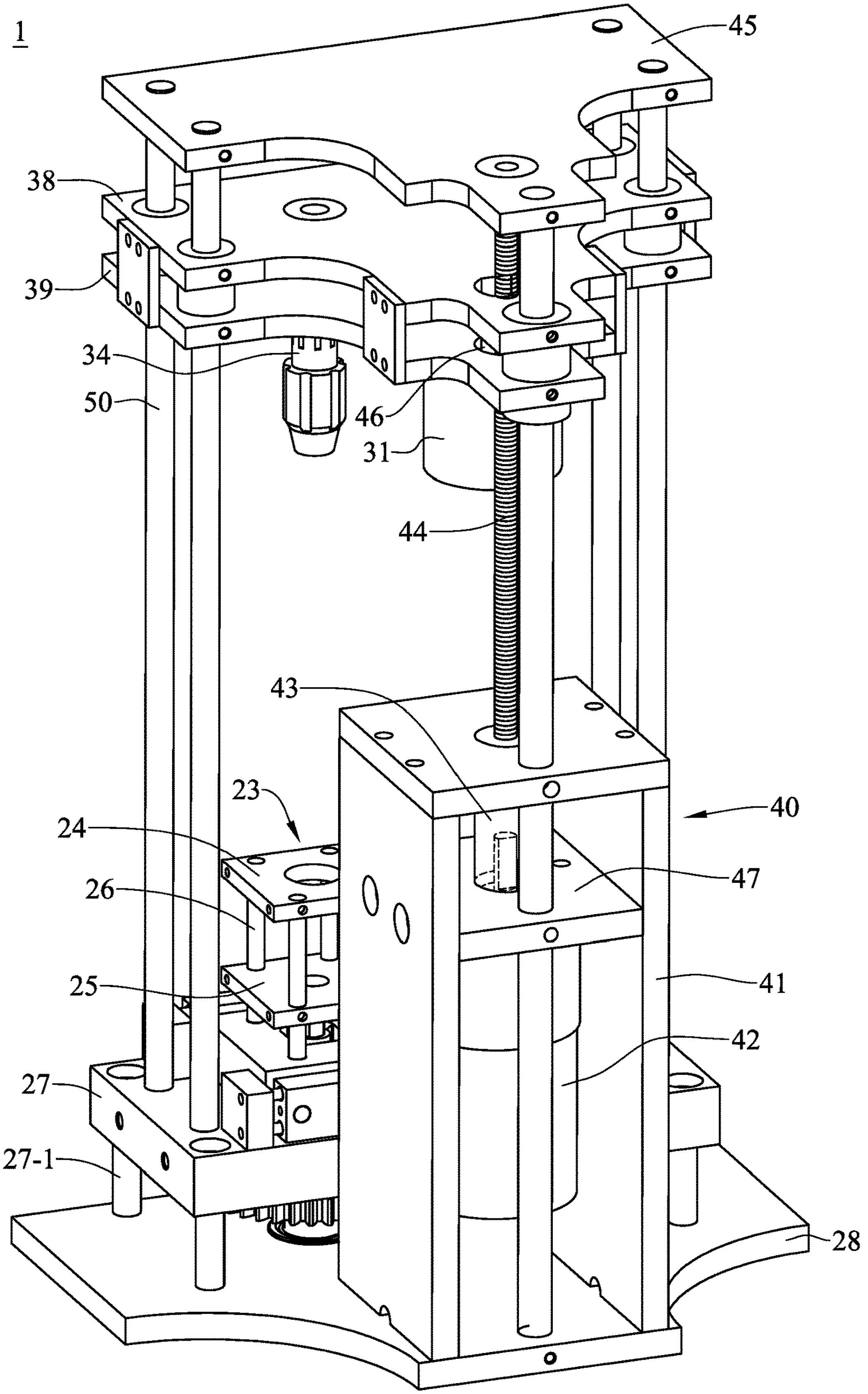
FIG. 2 is another view of FIG. 1.
Figure 3:
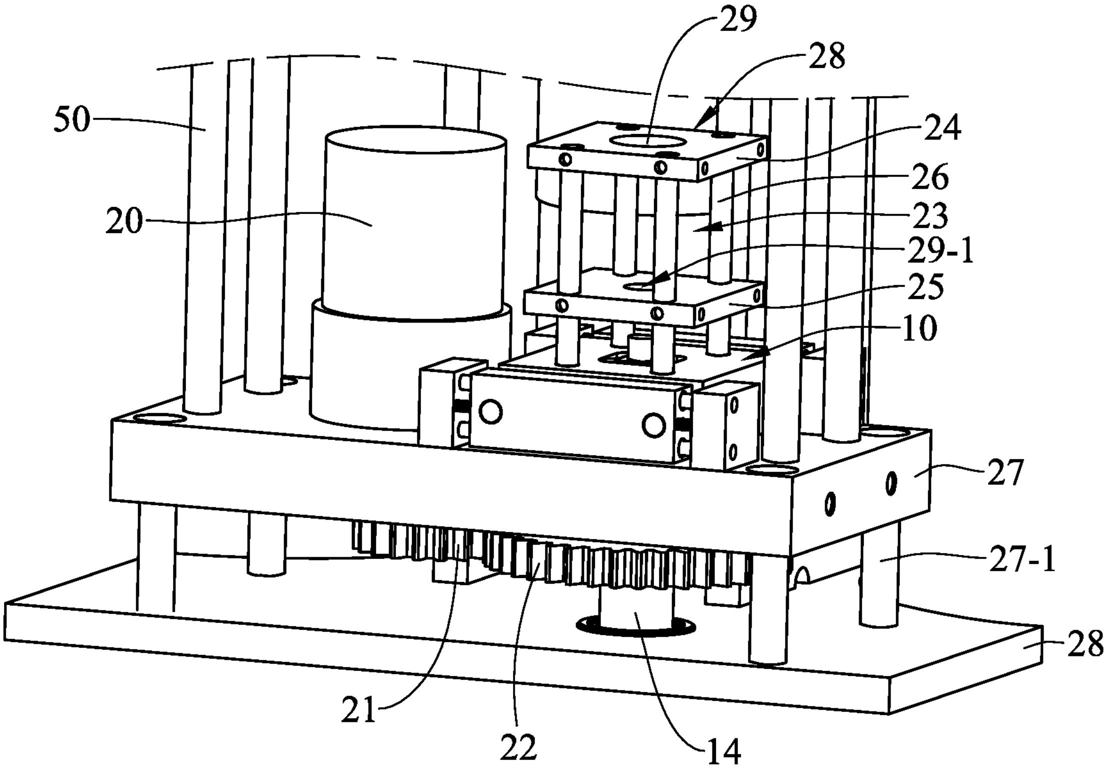
FIG. 3 is a schematic enlarged view of a lower-half portion of FIG. 1.
Figure 4:
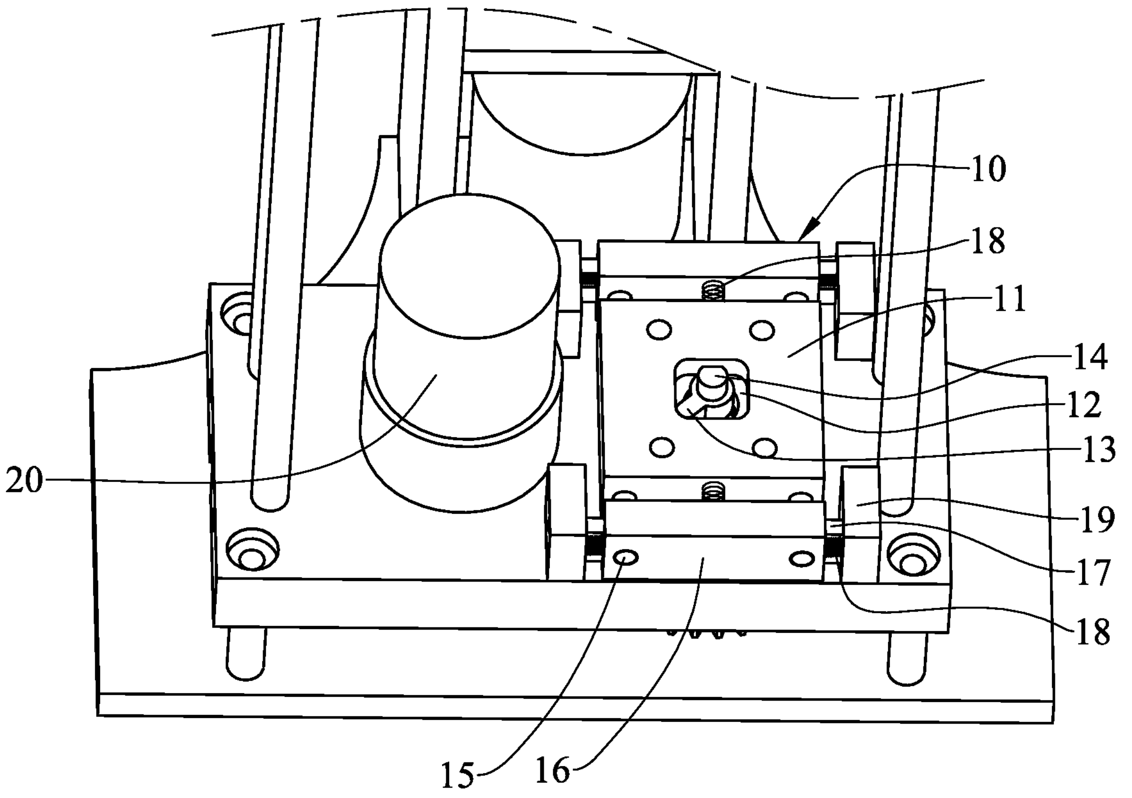
FIG. 4 is another view of FIG. 3.
Figure 5:
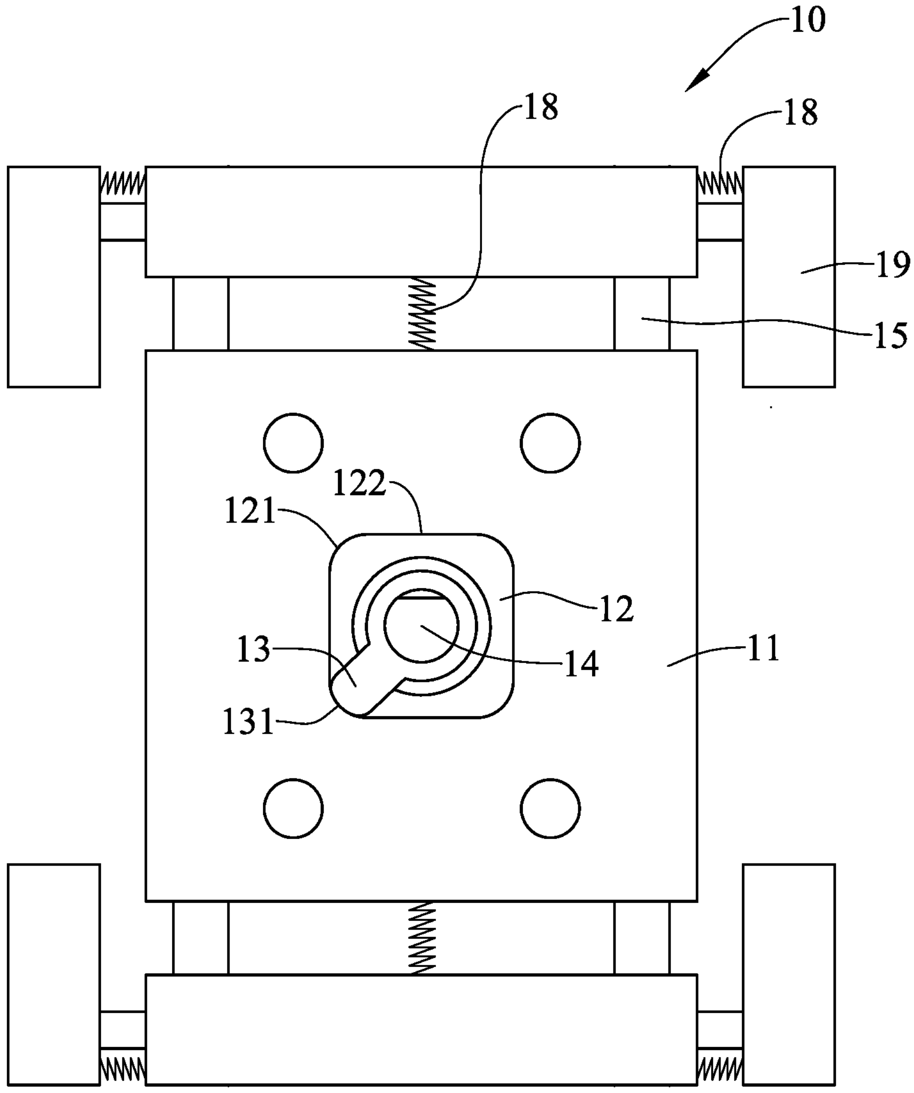
FIG. 5 is a top view of a portion of FIG. 4.

Refer to FIG. 1 through FIG. 5; where FIG. 1 is a schematic perspective view of a preferred grinding machine in accordance with the present disclosure, FIG. 2 is another view of FIG. 1, FIG. 3 is a schematic enlarged view of a lower-half portion of FIG. 1, FIG. 4 is another view of FIG. 3, and FIG. 5 is a top view of a portion of FIG. 4.

In order to set an innovative slight gyration module up, a grinding machine as shown in FIG. 1 is provided. The grinding machine 1 includes mainly a slight gyration module 10, a homogeneous-stick rotation module 30 and a homogeneous-stick vertical movement module 40.

The slight gyration module 10 includes a gyration base 11, a gyration hole 12, a gyration arm 13, a rotary shaft 14, at least one X-axial sliding rack 15, at least one Y-axial sliding block 16, at least one Y-axial sliding rack 17, at least one spring member 18 and at least one fixed block 19. The gyration arm 13 is fixed to a top end of the rotary shaft 14. The grinding machine 1 further includes a motor 20, a pinion 21 and a gear 22. By having the motor 20 to rotate the rotary shaft 14 through the pinion 21 and the gear 22, the gyration arm 13 of the slight gyration module 10 can slide along an inner contour of the gyration hole 12, such that the slight gyration module 10 can generate an expected slight gyration.

The homogeneous-stick rotation module 30 includes a rotary motor 31, a pulley set 32, a transmission belt 33 and a rotary shaft 34. A homogeneous stick 36 is connected to the rotary shaft 34 via a connector 35. The pulley set 32 is rotationally mounted between an upper fixed plate 38 and a lower fixed plate 39. The rotary motor 31 drives the pulley set 32 to rotate, and the rotation of the pulley set 32 is transmitted to the rotary shaft 34 through the transmission belt 33. While in a grinding operation, the homogeneous stick 36 is lowered into a homogeneous container 37 and rotated by the rotary shaft 34.

The homogeneous container 37 is positioned at a container carrier 23. The container carrier 23 is at least consisted of a carrier roof 24, a carrier base 25 and a plurality of connection columns 26 (four shown in the figure). These four connection columns 26 separate the carrier roof 24 from the carrier base 25 by a predetermined distance, and lower ends of these four connection columns 26 are fixed at the gyration base 11.

The homogeneous-stick vertical movement module 40 includes at least a supportive frame 41, a motor 42, a shaft coupler 43, a screw bar 44, a top plate 45, a nut 46 and a fixed frame 47. A top end of the screw bar 44 is rotationally mounted at the top plate 45, while a lower end of the screw bar 44 is connected to the motor 42*a* via the shaft coupler 43. The motor 42 is mounted under the fixed frame 47.

As shown in FIG. 2, it is clear to see that, in the homogeneous-stick vertical movement module 40, the top end of the screw bar 44 is rotationally located at the top plate 45, and the opposing lower end of the screw bar 44 applies the shaft coupler 43 to further connect with the motor 42. The nut 46 that pairs the screw bar 44 is fixed to the lower fixed plate 39. The screw bar 44 penetrates the upper fixed plate 38 and engages the nut 46. Since the nut 46 is fixed at the lower fixed plate 39, thus a central threaded hole of the nut 46 allows the screw bar 44 to penetrate the nut 46 as well we the lower fixed plate 39 in a screwing manner. When the motor 42 rotates the screw bar 44 to further drive the upper fixed plate 38 and the lower fixed plate 39 to move vertically and linearly, the entire homogeneous-stick rotation module 30 can thus move synchronously as well. By adjusting the position of the homogeneous stick 36 with respect to the homogeneous container 37, the homogeneous stick 36 can perform the grinding inside the homogeneous container 37.

As shown in FIG. 3, in the slight gyration module 10, the motor 20 rotates the pinion 21 and the gear 22 that meshes the pinion 21, and the gear 21 further rotates the rotary shaft 14, such that the container carrier 23 fixed on the slight gyration module 10 can perform gyration motion. In this embodiment, co-axial holes 29, 29-1 are constructed on central portions of the carrier roof 24 and the carrier base 25, respectively. While in performing the grinding, the homogeneous container 37 is held by these two holes 29, 29-1 in a penetration manner. In some other embodiments not shown here, more than one pair of the co-axial holes can be constructed on the carrier roof 24 and the carrier base 25, so that the grinding upon a plurality of homogeneous containers can be performed simultaneously. (Note: at this time, an appropriate modification upon the homogeneous stick 36 shall be introduced; for example, a fork-type homogeneous stick.) The motor 20 is mounted on the upper base frame 27. Four base pillars 27-1 are applied to fix the upper base frame 27 above the lower base frame 28, such that a room can be generated in between for installing the pinion 21 and the gear 22. Upper ends of five pillars 50 are fixed to the top plate 45, while lower ends of these five pillars 50 are fixed to the upper base frame 27. Each of these five pillars 50 penetrates both the upper fixed plate 38 and the lower fixed plate 39 in a loose manner, such that the upper fixed plate 38 and the lower fixed plate 39 as a whole can move vertically along the these five pillars 50.

As shown in FIG. 4 and FIG. 5, in the preferred embodiment, the slight gyration module 10 includes one gyration base 11, one gyration hole 12, one gyration arm 13, one rotary shaft 14, two X-axial sliding racks 15, two Y-axial sliding blocks 16, two Y-axial sliding racks 17, six spring members 18 and four fixed blocks 19. The gyration hole 12 is formed in the gyration base 11, preferred to be a square having four corners 121. As shown. Each of the corners 121 is arc-shaped. The gyration arm 13 has a free round end 131 for constantly contacting the inner contour 122 of the gyration hole 12. When the gyration arm 13 is rotated, the free round end 131 thereof would slide along the inner contour 122 of the square gyration hole 12, such that the gyration base 11 having the gyration hole 12 can be moved by the gyration arm 13. Namely, with the arrangement of the square hole 12 and the gyration arm 13 having the free round end 131 to slide along the inner contour 121 of the gyration hole 12, a cam mechanism is formed to have the gyration base 11 to undergo a slight gyration motion driven by the rotation of the gyration shaft 14. Upon a relevant arrangement, a 1-3 mm radius of gyration can be achieved by this slight gyration motion. Theoretically, (the radius of gyration)=(the length of the gyration arm 13)−(a half length of the gyration hole 12).

As shown in FIG. 5, the two X-axial sliding racks 15 penetrate the gyration base 11 individually so as to provide the gyration base 11 to move linearly along the two parallel X-axial sliding racks 15. Two opposing ends of the X-axial sliding rack 15 are fixed to two respective Y-axial sliding blocks 16. On the other hand, two opposing ends of each Y-axial sliding rack 17 are fixed to two respective fixed blocks 19. The two parallel Y-axial sliding racks 17 penetrate the respective two Y-axial sliding blocks 16 individually, such that, while in the gyration motion, the two Y-axial sliding blocks 16, the two X-axial sliding racks 15 and the gyration base 11 can undergo a linear motion 16 along the two parallel Y-axial sliding racks 17. Namely, with the X-axial sliding racks 15 and the Y-axial sliding racks 17, the gyration base 11 can undergo linear motion in both the X-axial direction and the Y-axial direction. Preferably, the linear motion in each direction is limited to a ±1-3 mm distance in the corresponding axial direction.

An upper end of the rotary shaft 14 is fixedly engaged with the gyration arm 13, while a lower end of the rotary shaft 14 is fixed to the gear 21 as the rotation output of the gear 21. Namely, in this embodiment, the motor 10 drives the rotary shaft 14 via the pinion 21 and the gear 21. In addition, as shown in FIG. 5, four of the six spring members 18 are mounted individually between the fixed blocks 19 and the neighboring ends of the corresponding Y-axial sliding blocks 16, while another two of the spring members 18 are mounted individually between the gyration base 11 and the neighboring sides of the corresponding Y-axial sliding blocks 16. These six spring members 18 are to elastically restrain the slight gyration motion of the gyration base 11.

Figure 6:
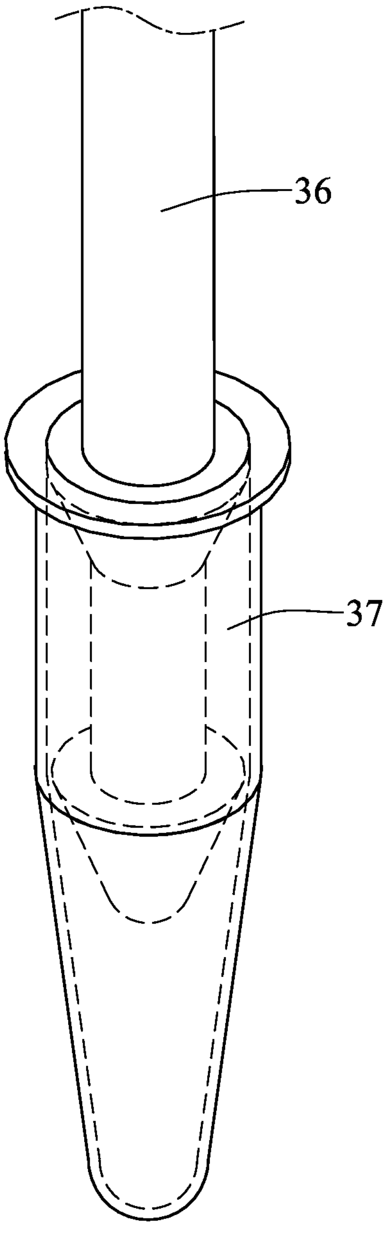
FIG. 6 is a schematic perspective view of a homogeneous container and a homogeneous stick in accordance with the present disclosure.

Referring now to FIG. 6, a schematic perspective view of the homogeneous container 37 and the homogeneous stick 36 is shown. In the grinding operation of this embodiment, the homogeneous stick 36 is lowered into the homogeneous container 37. Both the homogeneous container 37 and the homogeneous stick 36 have respective V-shape ends. While the V-shape end of the homogeneous stick 36 is lowered to position in the homogeneous container 37, these two sleeving V-shape ends are separated by a tiny slim space. When the homogeneous container 37 is positioned by the container carrier 23, the homogeneous stick 36 is lowered into the homogeneous container 37 by the homogeneous-stick vertical movement module 40, further the homogeneous stick 36 is rotated by the homogeneous-stick rotation module 30, and the slight gyration motion upon the homogeneous container 37 is performed by the slight gyration module 10, then a corresponding eccentric motion would occur between the homogeneous container 37 and the homogeneous stick 36 so as to carry out the grinding in the aforesaid tiny slim space between the homogeneous container 37 and the homogeneous stick 36. Upon such an arrangement, the grinding efficiency of the grinding machine can be substantially enhanced.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A grinding machine, comprising:

a slight gyration module for driving a homogeneous container to undergo an X-axial motion and a Y-axial motion, wherein the slight gyration module further includes at least a gyration base, a gyration hole, a gyration arm, a rotary shaft, an X-axial sliding rack, a Y-axial sliding block, a Y-axial sliding rack, a plurality of spring members and a fixed block, the gyration arm being fixed to an upper end of the rotary shaft, the X-axial sliding rack penetrating the gyration base, the Y-axial sliding rack penetrating the Y-axial sliding block, the fixed block positioning the Y-axial sliding rack, one of the spring members being mounted between the gyration base and the Y-axial sliding block, another one of the spring members being mounted between the Y-axial sliding block and the fixed block;

a homogeneous-stick rotation module for rotating a homogeneous stick in the homogeneous container so as to generate an eccentric motion between the homogeneous stick and the homogeneous container; and a homogeneous-stick vertical movement module for vertically moving the homogeneous stick with respect to the homogeneous container.

2. The grinding machine of claim 1, wherein the gyration hole is a square hole having four arc-shaped corners.

3. The grinding machine of claim 1, wherein the gyration arm has a free round end for constantly contacting an inner contour of the gyration hole; wherein, while the gyration arm rotates to drive the gyration base, a radius of gyration is a difference of a length of the gyration arm and a half length of the gyration hole.

4. The grinding machine of claim 3, wherein the radius of gyration is within 1-3 mm.

5. The grinding machine of claim 1, wherein the gyration base is able to undergo linear motion along the X-axial sliding rack and the Y-axial sliding rack, with ±1-3 mm distance in each of axial directions extending the X-axial sliding rack and the Y-axial sliding rack.

6. The grinding machine of claim 1, further including a motor, the motor driving the slight gyration module via a gear pair.

7. The grinding machine of claim 1, further including a container carrier located on the slight gyration module, the container carrier including a carrier roof, a carrier base and a plurality of connection columns.

8. The grinding machine of claim 7, wherein the carrier roof and the carrier base have a plurality of co-axial holes for holding a plurality of homogeneous containers so as to perform grinding upon the plurality of homogeneous containers.

9. The grinding machine of claim 1, wherein the homogeneous-stick rotation module further includes a rotary motor, a pulley set, a transmission belt and a rotary shaft, the rotary shaft being connecting to the homogeneous stick, the rotary motor rotating the rotary shaft via the transmission belt so as to rotate the homogeneous stick in the homogeneous container to perform grinding.

10. The grinding machine of claim 1, wherein the homogeneous-stick vertical movement module further includes a supportive frame, a motor, a shaft coupler, a screw bar, a top plate, a nut and a fixed frame, a top end of the screw bar being rotationally mounted at the top plate while a lower end of the screw bar is connected to the motor via the shaft coupler, the motor being mounted under the fixed frame.

11. The grinding machine of claim 10, wherein the nut engaging the screw bar is fixed at the lower fixed plate;

wherein, when the motor rotates the screw bar, the upper fixed plate and the lower fixed plate as a whole are driven to undergo a vertical linear motion so as to move the homogeneous-stick rotation module synchronously and to have the homogeneous stick able to perform grinding in the homogeneous container.

12. A slight gyration module, comprising:

a gyration base, having a gyration hole thereof;

a gyration arm, constantly contacting an inner contour of the gyration hole;

a rotary shaft, having an upper end thereof to fixed engage the gyration arm;

an X-axial sliding rack, penetrating the gyration base;

a Y-axial sliding rack, penetrating a Y-axial sliding block; and a fixed block, positioning fixedly the Y-axial sliding rack.

13. The slight gyration module of claim 12, wherein the X-axial sliding rack is fixed to the Y-axial sliding block.

14. The slight gyration module of claim 12, further including a plurality of spring members, one of the spring members being mounted between the gyration base and the Y-axial sliding block, another one of the spring members being mounted between the Y-axial sliding block and the fixed block.

15. The slight gyration module of claim 12, wherein the gyration hole is a square hole having four arc-shaped corners.

16. The slight gyration module of claim 12, wherein the gyration arm has a free round end for constantly contacting the inner contour of the gyration hole; wherein, while the gyration arm rotates to drive the gyration base, a radius of gyration is a difference of a length of the gyration arm and a half length of the gyration hole.

17. The slight gyration module of claim 16, wherein the radius of gyration is within 1-3 mm.

18. The slight gyration module of claim 12, wherein the gyration base is able to undergo linear motion along the X-axial sliding rack and the Y-axial sliding rack, with ±1-3 mm distance in each of axial directions extending the X-axial sliding rack and the Y-axial sliding rack.

19. The slight gyration module of claim 12, further including a motor, the motor driving the slight gyration module via a gear pair.

20. The slight gyration module of claim 12, further including a container carrier located on the slight gyration module, the container carrier including a carrier roof, a carrier base and a plurality of connection columns.

21. The slight gyration module of claim 20, wherein the carrier roof and the carrier base have a plurality of co-axial holes for holding a plurality of homogeneous containers so as to perform grinding upon the plurality of homogeneous containers.

* * * * *